United States Patent [19]

Ueoka et al.

[11] Patent Number: 4,956,493

[45] Date of Patent: Sep. 11, 1990

[54] PROCESS FOR PRODUCING METHACRYLIC ESTER

[75] Inventors: Masatoshi Ueoka; Syoichi Matsumoto, both of Himeji; Hiroshi Yoshida, Toyanaka; Masao Baba, Himeji, all of Japan

[73] Assignee: Nippon Shokubai Kagaku Kogyo Co., Ltd., Osaka, Japan

[21] Appl. No.: 181,369

[22] Filed: Apr. 14, 1988

[30] Foreign Application Priority Data

Apr. 16, 1987 [JP] Japan .................................. 62-91932
Aug. 6, 1987 [JP] Japan .................................. 62-195347

[51] Int. Cl.$^5$ ............................................. C07C 67/00
[52] U.S. Cl. ...................................... 560/208; 562/532
[58] Field of Search ......................... 560/208; 562/532

[56] References Cited

U.S. PATENT DOCUMENTS

| | | | |
|---|---|---|---|
| 3,776,947 | 12/1973 | Shimizu et al. | 560/208 |
| 4,060,545 | 11/1977 | Miller et al. | 560/208 |
| 4,223,161 | 9/1980 | Shaw et al. | 560/208 |
| 4,317,926 | 3/1982 | Sato | 560/208 |

FOREIGN PATENT DOCUMENTS

| | | |
|---|---|---|
| 0102642 | 3/1984 | European Pat. Off. . |
| 3308879 | 9/1983 | Fed. Rep. of Germany . |
| 58-192851 | 11/1983 | Japan . |
| 2096601 | 10/1982 | United Kingdom . |

OTHER PUBLICATIONS

European Search Report dated 1, 1988.

*Primary Examiner*—Paul J. Killos
*Attorney, Agent, or Firm*—Sherman and Shalloway

[57] ABSTRACT

A process for producing a methacrylic ester which comprises catalytically oxidizing isobutylene, tert-butanol, methacrolein or isobutyl aldehyde in a vapor phase; removing light-boiling substances form the resulting reaction product by distillation or stripping; extracting methacrylic acid from the resulting methacrylic acid aqueous solution using a saturated chain aliphatic hydrocarbon having 6 to 9 carbon atoms as a solvent; recovering the solvent from the obtained solvent solution of methacrylic acid; esterifying the resulting methacrylic acid by the reaction of it with a lower aliphatic alcohol or a lower alicyclic alcohol having 1 to 12 carbon atoms using a porous strongly acidic cation exchange resin as a catalyst for esterfication; and then subjecting the thus obtained esterification reaction product to a purification step.

8 Claims, 1 Drawing Sheet

PROCESS FOR PRODUCING METHACRYLIC ESTER

This invention relates to a process for producing a methacrylic ester, and more specifically, to a process for producing a methacrylic ester which comprises catalytically oxidizing isobutylene, tert-butanol, methacrolein or isobutyl aldehyde in a vapor phase and reacting the resulting methacrylic acid with an alcohol.

A process for producing methacrylic acid by catalytically oxidizing isobutylene, tert-butanol, methacrolein or isobutyl aldehyde in a vapor phase has been well known. In said catalytic vapor-phase oxidation reaction, methacrylic acid is obtained as a main substance and many other by-products are formed. These by-products not only cause troubles in a step of separating and purifying methacrylic acid but, when methacrylic acid is used as a starting material for producing a methacrylic ester, cause troubles in esterification step or have an adverse effect on qualities of the methacrylic ester. For instance, in case methacrylic acid obtained by a catalytic vapor-phase oxidation method is esterified with an alcohol in the presence of a cation exchange resin to prepare a methacrylic ester, a catalytic activity of the cation exchange resin decreases or qualities, e.g. color stability, of a methacrylic ester as a final product or products such as an emulsion formed from the methacrylic ester as a starting material worsen. This is principally ascribable to the by-products contained in methacrylic acid. Accordingly, various improvements have been proposed in, for example, CA (105)6959, CA (101) 38985 and EP 102642. In the processes proposed therein, high-quality methacrylic acid is produced by sequentially going through a large number of complicated steps comprising cooling a gas obtained by the catalytic vaporphase oxidation reaction, collecting the gas with water to form a methacrylic acid aqueous solution, removing light-boiling substances from said aqueous solution, then adding a bisulfite, extracting methacrylic acid with an aromatic hydrocarbon such as xylene or toluene as a solvent, separating the solvent, separating light-boiling substances, separating high-boiling substances and conducting purification by distillation. However, these processes require many complicated steps and devices. Moreover, in said catalytic vapor-phase oxidation, high-boiling carboxylic acids such as terephthalic acid and benzoic acid and relatively high-boiling by-products such as tarry substances result. As methacrylic acid is distilled off in the step of separating high-boiling substances, these by-products are deposited on the bottom of the column, making difficult the operation. At this time, concentration is controlled to such extent that the high-boiling substances are not deposited. Accordingly, a substantial amount of methacrylic acid is left in the high-boiling substances withdrawn from the bottom of the column as a waste liquor in the step of separating the high-boiling substances, thereby decreasing the yield of the final product and increasing weight on treatment of the waste liquor.

Meanwhile, a process for producing a methacrylic ester by reacting methacrylic acid with an alcohol in the presence of a cationic exchange resin is also known (US 3,776,947, CA (94) 16332 and DE 3,308,879). Usually in such process, after methacrylic acid is reacted with an alcohol in the presence of a cation exchange resin, an esterification reaction product is distilled, unreacted methacrylic acid is withdrawn from the bottom of the column and returned to the esterification reactor, a mixture of a methacrylic ester, an alcohol and water is distilled off, the distillate is subjected to extraction and distillation to obtain a methacrylic ester as a final product and the alcohol is recovered and reused. When the by-products contained in the starting methacrylic acid, polymerized products of methacrylic acid or polymerized products of the methacrylic ester are accumulated as noted earlier, troubles such as clogging of the cation exchange resin layer and decrease in catalytic activity occur. For this reason, it is also necessary that methacrylic acid purified through the aforesaid complicated steps and devices is used as an esterification reaction starting material and before returned to the esterification reactor, the unreacted methacrylic acid recovered after the esterification reaction is treated with a thin-layer evaporator, etc. to remove the high-boiling impurities and polymerized products. On this occasion, however, since the polymerized products or impurities are gradually deposited as solid matters on treating devices such as the thin-layer evaporator, etc., there is a need to sometimes stop the devices and remove the deposits.

Relative to the conventional process for producing the methacrylic ester from the high-quality methacrylic acid as a starting material which undergoes a large number of complicated steps and devices, a process for producing a methacrylic ester has been also shown which comprises obtaining a solvent phase containing methacrylic acid from a methacrylic acid aqueous solution using various hydrocarbons having 5 to 17 carbon atoms as an extraction solvent, reacting the solvent phase with an alcohol in the presence of a catalyst for esterification, washing the esterification reaction product with water or salt water to remove impurities, and purifying the residue by distillation (CA (81) 170,210). In this process, a step up to formation of methacrylic acid as an esterification reaction starting material is simplified, and the total amount of methacrylic acid formed by the catalytic vapor-phase oxidation reaction is supplied to the esterification reaction step. Therefore, a loss of methacrylic acid does not occur before the esterification reaction. However, since the reaction product is neutralized with a sodium carbonate aqueous solution after the esterification reaction, the alcohol is recovered but unreacted methacrylic acid is discarded, posing problems with both the loss of methacrylic acid and the treatment of waste liquor. Moreover, as methacrylic acid containing a large amount of the solvent is supplied to the esterification reaction step, the size of the esterification reactor goes large compared to the amount of the final product and the amount of the treated solution per unit weight of the esterification catalyst becomes large; the efficiency is therefore low.

According to the knowledge of the present inventors, it has been made clear that as the operation is run continuously for a longer period of time, the catalytic activity lowers, causing troubles.

Besides, the present inventors have found the following fact. That is, a trace amount of by-product acetonylacetone is contained in methacrylic acid yielded by the catalytic vapor-phase oxidation reaction, and condensed and cyclized into dimethylfuran in the esterification reaction. If dimethylfuran is contained in the methacrylic ester as a final product, it adversely affects a color of said product or a secondary product, e.g. an emulsion obtained from said product. A conversion of dimethylfuran from acetonylacetone is not so high. However, in recovering and reusing unreacted methacrylic acid, acetonylacetone is entrained and acculumated in the system, which results in increasing the amount of dimethylfuran formed. In addition, because dimethylfuran is low in specific degree of volatility with a lower methacrylic ester such as methyl methacrylate in particular, it is hard to separate The aforesaid prior documents do not describe this fact, nor do they disclose effective means taking account of this fact.

Accordingly, an object of this invention is to remedy the foregoing defects encountered in the conventional processes, i.e. to provide a process for producing a methacrylic ester, which can simplify steps and devices, reduce an amount of a waste liquor, attain long-term continuous operation and afford a high-quality methacrylic ester in high yield.

The present inventors have made extensive studies and as a result, discovered that the object of this invention can be achieved by using saturated chain aliphatic hydrocarbons having 6 to 9 carbon atoms as an extraction solvent in the step of extracting methacrylic acid from a methacrylic acid aqueous solution and a porous strongly acidic cation exchange resin as a catalyst for esterification in the esterification step.

This invention is thus to provide a process for producing a methacrylic ester which comprises catalytically oxidizing isobutylene, tert-butanol, methacrolein or isobutyl aldehyde in a vapor phase; removing lightboiling substances from the resulting reaction product by distillation or stripping; extracting methacrylic acid from the resulting methacrylic acid aqueous solution using a saturated chain aliphatic hydrocarbon having 6 to 9 carbon atoms as a solvent; recovering the solvent from the obtained solvent solution of methacrylic acid; esterifying the resulting methacrylic acid by the reaction of it with a lower aliphatic alcohol or a lower alicyclic alcohol having 1 to 12 carbon atoms using a porous strongly acidic cation exchange resin as a catalyst for esterification; and then subjecting the thus obtained esterification reaction product to a purification step.

In this invention, as in the prior processes, isobutylene, tert-butanol, methacrolein or isobutyl aldehyde is first catalytically oxidized in a vapor phase, the obtained reaction product gas is cooled and collected with water, and the resulting aqueous solution is subjected to a distillation or stripping step to remove small amounts of light-boiling substances such as methacrolein and acetone in the aqueous solution.

Subsequently, the methacrylic acid aqueous solution is fed to the step of extracting the solvent where said aqueous solution is separated into a solvent phase containing methacrylic acid and an aqueous phase. On that occasion, a saturated chain aliphatic hydrocarbon having 6 to 9 carbon atoms is used as an extraction solvent. In case of using aromatic hydrocarbons such as xylene and toluene, the ratio of the concentration of high-boiling impurities to the concentration of methacrylic acid in the solvent phase after extraction is high, posing problems with precipitation of solid matters considered to attribute to the aforesaid highboiling impurities and decrease in catalytic activity of the catalyst for esterification. Moreover, the high proportion of acetonylacetone gives problems with qualities of the products as stated above. Nevertheless, when using the saturated chain aliphatic hydrocarbons having 6 to 9 carbon atoms in accordance with this invention, the ratio of the concentration of high-boiling impurities to the concentration of methacrylic acid in the solvent phase after extraction becomes low, and the combined use of the porous strongly acidic cation exchange resin as a catalyst for esterification, which will be later described, leads to solution of problems with the complicated steps and devices found in the conventional processes.

Concrete examples of the saturated chain aliphatic hydrocarbons having 6 to 9 carbon atoms are hexane, heptane, octane and nonane, and they may be linear or branched hydrocarbons. A mixture of them is also available If the saturated chain aliphatic hydrocarbons having 6 to 9 carbon atoms are however used as an extraction solvent, an extraction rate of methacrylic acid is somewhat low, and the amount of the extraction solvent is therefore a bit larger. It is therefore effective also that to reduce the amount of the extraction solvent, a mixture of the saturated chain aliphatic hydrocarbon having 6 to 9 carbon atoms and the other solvent, e.g. a methacrylic ester, an aromatic hydrocarbon such as xylene or toluene is used as an extraction solvent. As to the mixing ratio in this case, it is advisable that the saturated chain aliphatic hydrocarbon having 6 to 9 carbon atoms is contained in an amount of 50% by weight or more.

The extraction may be conducted under the ordinary conditions. For example, if a usual countercurrent contact device is used and the temperature is from room temperature to 70° C. and a weight ratio of the extraction solvent to the methacrylic acid aqueous solution is 0.5 to 1.5, good extraction results are obtained.

A solvent phase containing methacrylic acid has been so far subjected, as seen in CA (105) 6959 to a great many complicated steps, such as a step of separating the solvent, a step of separating light-boiling substances, a step of separating high-boiling substances and a step of purification by distillation to obtain high-quality methacrylic acid which is used as a starting material for esterification reaction. This invention however requires such simple steps that a solvent phase containing methacrylic acid after a solvent extracting step is fed to a simple solvent separating step consisting only of distillation where the solvent phase is separated into crude methacrylic acid and the solvent, the solvent is recovered and recycled, and the crude methacrylic acid is meanwhile fed to an esterifying step where methacrylic acid is reacted with a lower aliphatic alcohol having 1 to 12 carbon atoms in the presence of a catalyst to produce a methacrylic ester.

As starting methacrylic acid in the esterifying step, a mixture of said crude methacrylic acid and recovered methacrylic acid fed from the subsequent step is also available. The crude methacrylic acid contains small amounts of high-boiling carboxylic acids such as terephthalic acid, benzoic acids, etc. Nevertheless, these high-boiling carboxylic acids are esterified and the carboxylic acid esters are increased in solubility in the methacrylic ester compared to the carboxylic acids. Consequently, they are not deposited and clogging of the esterification catalyst layer is preventable in the esterifying step.

Concrete examples of the lower aliphatic alcohol having 1 to 12 carbon atoms, used in the esterifying step, include methanol, ethanol, propanol, butanol, 2-ethyl-hexanol and cyclohexanol, and they may be either linear or branched.

In this invention, a porous strongly acidic cation exchange resin is used as a catalyst in the esterifying step. Said catalyst shows improved resistance to organic pollution and keeps sufficient catalytic ability. However, other strongly acidic cation exchange resins have a defect that as the time lapses, their catalytic activity decreases and long-term operation becomes difficult. Moreover, as stated above, the present inventors have found that by-product acetonylacetone formed by the catalytic vapor-phase oxidation reaction is condensed and cyclized into dimethylfuran in the esterification reaction and when dimethylfuran is contained in a methacrylic ester as a final product, it adversely affects a color of the product or a secondary product obtained from said product, such as an emulsion. It has been further found that when the porous strongly acidic cation exchange resin is used in the esterification reaction, dimethylfuran is less formed in comparison with the use of a gel-type cation exchange resin.

As the porous strongly acidic cation exchange resin, a resin having a degree of crosslinking of 2 to 16%, a specific surface area of 0.2 to 50 $m^2/g$, a porosity of 0 to 1.0 ml/g and an average pore diameter of 100 to 600 Å is preferable. Concrete examples of the porous strongly acidic cation exchange resin are Duolite ES-26 (a tradename for a product of Sumitomo Chemical Co., Ltd.); PK-208, PK-216 and PK-228 (tradenames for products of Mitsubishi Chemical Industries, Ltd.); MSC-1 and 88 (a tradename for a product of Dow Chemical Co.); and Amberlyst 16 (a tradename for a product of Rohm & Haas Co.).

The esterification reaction is performed in a liquid phase at a temperature of 50 to 110° C. in a suspended bed or a fixed bed. As is ordinarily done, a polymerization inhibitor can be used in the process of this invention too. Examples of the polymerization inhibitor include hydroquinone, methoxyhydroquinone, methylene blue and phenothiazine. If the reaction is run in the presence of molecular oxygen, the effect of the polymerization inhibitor can be further increased.

It is possible that the thus obtained esterification reaction product is treated in a usual manner, methacrylic acid and alcohol are recovered for reuse and a methacrylic ester is obtained as a final product. Besides, as stated above, the high-boiling carboxylic acids contained in methacrylic acid supplied from the solvent extracting step are esterified in the esterification reaction step and solubility of the carboxylic acid esters are increased in comparison with that of the carboxylic acids. As a result, in removing the polymerized products or impurities in methacrylic acid through a vacuum evaporator, precipitation of them as solid matters does not occur or is minimized, thereby enabling long-term continuous operation.

Where the alcohol used in the esterification reaction step is a lower aliphatic alcohol having 1 to 4 carbon atoms, it is effective that in the purifying step, the esterification reaction product is distilled by an evaporator and the distillation bottoms of the evaporator are recycled to the esterification reaction step, while the distillate of the evaporator is cooled and separated into an oil phase and an aqueous phase, the alcohol is separated from the aqueous phase by distillation and recycled to the esterification reaction step and a methacrylic ester is purified from the oil phase by distillation. On this occasion, the esterification reaction product is sent to the evaporator and separated into the distillation bottoms composed mainly of methacrylic acid and the distillate formed by the reaction and composed mainly of the methacrylic ester, water and the alcohol. The distillation bottoms are recovered and recycled to the esterification reaction step. Preferably during the recycling, part or the whole of the distillation bottoms are distilled to remove polymerized products or impurities in methacrylic acid, preventing accumulation of them in the system. As a result, troubles such as clogging of the esterification catalyst layer are preventable. Especially the removal of high-boiling impurities can prevent accumulation of acetonylacetone as a source of generating dimethylfuran in the esterification reaction, and the methacrylic ester as a final product having a good color stability or a secondary product using the final product as a starting material and having also a good color stability is obtainable.

Meanwhile, the distillate from the evaporator is cooled and separated into an oil phase and an aqueous phase. The alcohol is separated from the aqueous phase by distillation and recycled to the esterification reaction step. From the oil phase, the methacrylic ester is purified by distillation and obtained as a final product. At this time, as a trace amount of methacrylic acid is entrained in the distillate leaving the evaporator, it does not pose a problem with the yield of methacrylic acid. As said methacrylic acid can be recovered from the aforesaid oil phase in the step of purifying the methacrylic ester by distillation, it may be recycled to the esterification reaction step. Moreover, by using a fractionating column instead of the evaporator, the amount of methacrylic acid entrained in the distillate can be reduced to a trace.

Where the alcohol used in the esterification reaction step is a lower aliphatic alcohol having 5 or more carbon atoms, the boiling point of the ester formed in the esterification reaction goes higher than the boiling points of methacrylic acid and alcohol. In this instance, a reaction-distillation method is preferable. Namely, water formed by the esterification reaction is distilled off from a distillation column juxtaposed with the reactor and removed outside the system, advancing the reaction. To prevent distillation of methacrylic acid, it is advisable to feed part of the alcohol from the top of the distillation column. The distillation bottoms of the reactor are fed to a light-boiling substance separation column, and unreacted alcohol and methacrylic acid are distilled off and recycled to the esterification reaction step. The distillation bottoms of the light-boiling separation column are fed to the high-boiling substance separation column, and purified methacrylic ester is obtained from the top of the column. The distillation bottoms of the high-boiling substance separation column are recovered, and part or the whole thereof are sent to a thin-layer evaporator to remove polymerized products or impurities, preventing accumulation thereof in the system.

By referring to the accompanying drawing, this invention is explained in more detail.

The accompanied drawing is a flow sheet showing a suitable embodiment of this invention in case of using a lower aliphatic alcohol having 1 to 4 carbon atoms.

A methacrylic acid aqueous solution obtained in the reaction step of catalytically oxidizing isobutylene, tert-butanol, methacrolein or isobutyl aldehyde in a vapor phase is fed to a methacrylic acid extracting column (1) via a line 1. On the other hand, an extraction solvent is fed to the methacrylic acid extracting column (1) via a line 2 and countercurrently contacted with the methacrylic acid aqueous solution, and methacrylic acid is extracted into a solvent phase. An aqueous phase is withdrawn from a line 3 and properly treated. The solvent phase containing methacrylic acid is fed from the line 4 to a solvent separating column (2) where the solvent is recovered as a distillation fraction and returned to the methacrylic acid extracting column (1) via the line 2. In the meantime, crude methacrylic acid is withdrawn from the bottom of the solvent separating column (2), passes through a line 6 and fed to an esterification reactor (3) together with recovered methacrylic acid fed through a line 12. The esterification reactor (3) is filled with a porous strongly acidic cation exchange resin, and methacrylic acid is esterified there with an alcohol fed from a line 7. The esterification reaction product composed of methacrylic acid, methacrylic ester, alcohol and water is fed to an evaporator (4) via a line 8 and distilled. Unreacted methacrylic acid, polymerized products and high-boiling impurities accompanied with the starting methacrylic acid are withdrawn from the bottom of the evaporator (4), and part or the whole thereof are sent to a distillation column (5) juxtaposed with a thin-layer evaporator (6) through a line 10. The polymerized products and the high-boiling impurities are withdrawn from the bottom of the thinlayer evaporator (6) and removed outside the system via a line 11. Methacrylic acid distilled off from the top of the distillation column (5) is recycled to the esterification reactor (3) and reused as a starting material for esterification. A methacrylic ester, an alcohol and water are distilled off from the top of the evaporator (4) and fed to an oil-water separator (7) via a line 9. An aqueous phase containing the alcohol is fed to an alcohol recovering column (8) via a line 13 and distilled. The alcohol is recovered from a line 15 and can be recycled to the esterification reactor (3). From the bottom of the alcohol recovering column (8), water is withdrawn and removed as a waste liquor outside the system via a line 16. An oil phase containing a methacrylic ester, separated in the oil-water separator (7), is fed to a light-boiling substance separating column (9) via a line 17 and distilled. The light-boiling fraction distilled off from a line 18 is separated into an aqueous phase and an oil phase. The oil phase is recycled to a light-boiling substance separating column (9) and the aqueous phase to an alcohol recovering column (8) via a line 19. In case separation of the fraction of the light-boiling separating column (9) into the aqueous phase and the oil phase is insufficient, it is advisable to conduct said separation by adding part of the distillation bottoms of the alcohol recovering column or mixing the fraction with the fraction of the evaporator. A methacrylic ester is withdrawn from the bottom of the light-boiling substance separating column (9) and fed to a high-boiling substance separating column (10) via a line 20. The methacrylic ester is fractionated there and obtained as a final product through a line 21. The high-boiling substances withdrawn from the bottom of the high-boiling separating column (10) are taken out via a line 22. Where unreacted methacrylic acid is contained in the high-boiling substances, it is recovered and recycled to the esterification reactor (3) via the line 22.

The following Examples and Comparative Examples illustrate this invention in more detail.

EXAMPLE 1

Isobutylene was subjected to catalytic vaporphase oxidation reaction with air in the presence of a steam using a molybdenum-type catalyst. A reaction product gas was cooled and condensed and light-boiling substances such as methacrolein, etc. were removed by distillation to afford 12.5 kg/hr of a methacrylic acid aqueous solution containing 35% by weight of methacrylic acid, 5.3% by weight of acetic acid, 2.0% by weight of phthalic acids (o-, m- and o-phthalic acids), 1.2% by weight of maleic acid and 1.5% by weight of a tarry substance.

The methacrylic acid aqueous solution was fed from an upper portion of an extraction column (1) consisting of a rotary disc column having an inner diameter of 70 mm and a total height of 1,800 mm, and 16.4 kg/hr of n-heptane was fed from a lower portion of the extraction column (1). The countercurrent extraction was continuously performed. The extraction procedure was run at room temperature under normal pressures. After the extraction reached sufficient extraction equilibrium, 20.8 kg/hr of an n-heptane phase containing methacrylic acid was obtained from the upper portion of the extraction column and 8.1 kg/hr of an aqueous phase from the lower portion of the extraction column, respectively. Formation of a scum was not observed in the boundary between the two layers of the extraction column. The resulting n-heptane phase was fed to a 15th tray of a solvent separating column (2) (inner diameter 6 inches, 30 sieve trays, made of SUS 304), and distilled at a column top pressure of 105 mmHg and a reflux ratio of 1.0. n-Heptane distilled off from the top of the column was recycled to the extraction column for reuse. From the bottom of the solvent separating column, 99.7% by weight of methacrylic acid was obtained at a rate of 4.35 kg/hr.

To an esterificatioan reactor (3) filled with 20.6 liters of a porous strongly acidic cation exchange resin (dry) having a degree of crosslinking of 8%, a specific surface area of 4 m$^2$/g (BET method), a porosity of 0.1 ml/g and an average pore diameter of 300 Å was fed a starting material composed of said methacrylic acid, recovered methacrylic acid to be described later, fresh methanol and recovered methanol to be described later (composition: 44.65% by weight of methacrylic acid, 8.90% by weight of methanol, 43.17% by weight of methyl methacrylate, 1.64% by weight of water, 1.65% by weight of other substances and 225 ppm of acetonylacetone) at a rate of 26.65 kg/hr. The esterification reaction was conducted at 90° C. to obtain an esterification reaction product (composition: 28.44% by weight of methacrylic acid, 2.84% by weight of methanol, 61.93% by weight of methyl methacrylate, 5.01% by weight of water, 1.79% by weight of other materials, 221 ppm of acetonylacetone and 4 ppm of dimethylfuran).

The esterification reaction product was fed to an evaporator (4) and distilled under normal pressures to obtain 6.68 kg/hr of a fraction. Part of the distillation bottoms withdrawn from the bottom of the evaporator (4) were fed to a distillation column (5) juxtaposed with a thin-layer evaporator (6) at a rate of 1.50 kg/hr, and 0.06 kg/hr of a waste oil was withdrawn from the bottom of the thin-layer evaporator and discarded. 19.91 kg/hr of the recovered methacrylic acid obtained by mixing the remaining distillation bottoms of the evaporator (4) and the fraction of the distillation column (5) was recycled to the inlet of the esterification reactor.

The distillate of the evaporator (4) was separated into an oil phase and an aqueous phase in an oil-water separator (7). The composition of the oil phase was 1.15% by weight of methacrylic acid, 4.00% by weight of methanol, 92.40% by weight of methyl methacrylate and 2.45% by weight of water. The composition of the aqueous phase was 0.16% by weight of methacrylic acid, 27.53% by weight of methanol, 5.23% by weight of methyl methacrylate and 67.09% by weight of water.

Subsequently, 5.54 kg/hr of the oil phase was fed to a light-boiling substance separating column (9) (column diameter 7.5 cm, a glass Oldershaw distillation column having 20 steps), and the distillation was performed at a column top temperature of 52° C. and a column top pressure of 300 mmHg to obtain 5.13 kg/hr of distillation bottoms. Of the distillation fractions, the oil phase was recycled again to the top of the light-boiling separating column, and 0.41 kg/hr of the aqueous phase was fed to an alcohol recovering column (8) (column diameter 5.0 cm, a glass Oldershaw distillation column having 20 steps). At this time, methanol, water and methyl acrylate were not found in the distillation bottoms.

Further, the distillation bottoms of the light-boiling substance separating column (9) were fed to a high-boiling substance separating column (10) (column diameter 10 cm, a glass Oldershaw distillation column having 15 steps). The distillation was performed at a column top temperature of 46° C., a column bottom temperature of 66° C. and a column top pressure of 100 mmHg with 10 supply steps. Thus, purified methyl methacrylate was obtained from the top of the column at a rate of 5.00 kg/hr and the distillation bottoms from the bottom of the column at a rate of 0.13 kg/hr respectively. The purity of the resulting purified methyl methacrylate was 99.99% by weight. An emulsion obtained by emulsion polymerizing the purified methyl methacrylate had a good color stability.

On the other hand, the aqueous phases of the distillates of the evaporator (4) and the light-boiling separating column (9) were fed to the alcohol recovering column (8) at a rate of 1.55 kg/hr. The distillation was conducted at a column top temperature of 66° C., a column bottom temperature of 103° C. and normal pressure with 10 supply steps to obtain 0.65 kg/hr of a distillate and 0.90 kg/hr of distillation bottoms. The distillation bottoms contained only 0.2% by weight of methacrylic acid and methanol and methyl methacrylate were not found therein.

During the 60-day continuous operation, the aforesaid esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.0%. These results show that the process of this invention can fully withstand the long-term operation.

EXAMPLE 2

The esterification reaction and purification were carried out as in Example 1 except that n-hexane was used instead of n-heptane as an extraction solvent. The purity of the resulting purified methyl methacrylate was 99.99% by weight. Further, an emulsion obtained by emulsion polymerizing the purified methyl methacrylate had a good color stability.

During the 60-day continuous operation, the aforesaid esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.5%. These results show that the process of this invention can fully withstand the long-term operation.

EXAMPLE 3

The esterification reaction and purification were performed as in Example 1 except that n-octane was used instead of n-heptane as an extraction solvent. The purity of the resulting purified methyl methacrylate was 99.99% by weight. An emulsion obtained by emulsion polymerizing the purified methyl methacrylate had a good color stability.

During the 60-day continuous operation, the esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.3%. These results show that the process of this invention can fully withstand the long-term operation.

EXAMPLE 4

The esterification reaction and purification were performed as in Example 1 except that butanol was used instead of methanol and the reaction temperature was changed from 90° C. to 100° C. The purity of the resulting purified butyl methacrylate was 99.90% by weight.

During the 60-day continuous operation, the aforesaid esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.5%. These results reveal that the process of this invention can fully withstand the long-term operation.

EXAMPLE 5

The esterification reaction and purification were carried out as in Example 1 except that 10 kg/hr of a solvent mixture of n-heptane and methyl methacrylate (weight ratio 60:40) was fed from the lower portion of the extraction column instead of 16.4 kg/hr of n-heptane as an extraction solvent. The purity of the resulting purified methyl methacrylate was 99.99% by weight. An emulsion obtained by emulsion polymerizing the purified methyl methacrylate had a good color stability.

During the 60-day continuous operation, the esterification reactor, fractionating column and other devices did not give rise to troubles ascribable to polymerized products. As to the performance of the cation exchange resin as a catalyst for esterification reaction, the conversion of methacrylic acid remained unchanged before and after operation. The ion exchange capacity was decreased by only 3.2%. These results reveal that the process of this invention can fully withstand the long-term operation.

EXAMPLE 6

The esterification reaction and purification were performed as in Example 1 except that instead of the evaporator (4) a glass Oldershaw distillation column having a column diameter of 10 cm and provided with 15 steps was used so as not to incorporate methacrylic acid into the fraction of the distillation column. The purity of the resulting purified methyl methacrylate was 99.99% by weight. An emulsion obtained by emulsion polymerizing the purified methyl methacrylate had a good color stability.

During the 60-day continuous operation, the esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.3%. These results reveal that the process of this invention can fully withstand the long-term operation.

EXAMPLE 7

A 100-liter stainless steel esterification reactor provided thereinside with a baffle, at its bottom with a reaction liquid withdrawing pipe and at its upper portion with a starting material feed pipe, a distillation column and a stirrer was filled with 18 liters of the same ion exchange resin as used in Example 1 and charged with 70 liters of a starting material comprising methacrylic acid formed in the same way as in Example 1, recovered methacrylic acid to be described later, fresh 2-ethylhexanol and recovered 2-ethylhexanol to be described later (composition: 36.52% by weight of methacrylic acid, 49.69% by weight of 2-ethylhexanol, 11.80% by weight of 2-ethylhexyl methacrylate and 0.69% by weight of water). The esterification reaction started at a temperature of 90° C. and a reactor inside pressure of 70 mmHg.

In the esterification reaction, the starting solution was fed from the starting material feed pipe disposed at the upper portion of the reactor at a rate of 36.60 kg/hr, and 2-ethylhexanol was fed from the top of the distillation column at a rate of 18.05 kg/hr. The solution distilled off from the top of the distillation column disposed at the upper portion of the esterification reactor was separated into an oil phase (0.28 kg/hr) and an aqueous phase (2.45 kg/hr). The oil phase was recycled to the esterification reaction system, and the aqueous phase was removed outside the system. Meanwhile, in order to keep the amount of the solution in the reactor at 70 liters during the reaction, the esterification reaction product (composition 6.46% by weight of methacrylic acid, 40.45% by weight of 2-ethylhexanol, 52.37% by weight of 2-ethylhexyl methacrylate and 0.71% by weight of water) was continuously withdrawn from the bottom of the esterification reactor. The conversion of methacrylic acid was 74.8% and the conversion of 2-ethylhexanol was 41.7%. The amount of methacrylic acid in the aqueous phase removed outside the system was only a trace amount.

Subsequently, the esterification reaction product was fed to a light-boiling substance separating column and distilled. From the top of the column, 26.63 kg/hr of a fraction comprising unreacted methacrylic acid, 2-ethylhexanol, etc. (composition: 12.66% by weight of methacrylic acid, 79.28% by weight of 2-ethylhexanol, 6.67% by weight of 2-ethylhexyl methacrylate and 1.39% by weight of water) was recovered and returned to the esterification reactor.

The distillation bottoms of the light-boiling substance separating column were fed to a high-boiling substance separating column at a rate of 25.56 kg/hr, and purified 2-ethylhexyl methacrylate having a purity of 99.0% by weight was obtained from the top of the column at a rate of 22.63kg/hr. The distillation bottoms of the high-boiling substance separating column were withdrawn at a rate of 2.93 kg/hr, and part thereof were fed to a thin-layer evaporator. From the bottom of the thin-layer evaporator, a waste oil was withdrawn at a rate of 0.49 kg/hr and discarded.

During the 60-day continuous operation, the esterification reactor, fractionating column and other devices did not give rise to troubles ascribable to polymerized products. As to the performance of the cation exchange resin as a catalyst for esterification reaction, the conversion of methacrylic acid remained unchanged before and after operation, and the ion exchange capacity was decreased by only 3.0%. These results reveal that the process of this invention can fully withstand the long-term operation.

COMPARATIVE EXAMPLE 1

The esterification reaction and purification were performed as in Example 1 except that a gel-type strongly acidic cation exchange resin was filled instead of the porous strongly acidic cation exchange resin so that the overall exchange capacity became equal. The purity of the resulting purified methyl methacrylate was 99.99% by weight. However, an emulsion obtained by emulsion polymerizing the purified methyl methacrylate was no doubt inferior in color stability to those formed in Examples 1 to 3. Moreover, the conversion of methacrylic acid in the esterification reactor was gradually decreased, and the continuous operation had to be stopped only in 2 weeks. After the operation was over, the overall exchange capacity of the cation exchange resin was measured, and it was found to be decreased by 55% in comparison with that before operation (the ion exchange resin having such exchange capacity is clearly no longer usable).

COMPARATIVE EXAMPLE 2

The esterification reaction and purification were performed as in Example 1 except that methacrylic acid obtained by further purifying methacrylic acid withdrawn as the distillation bottom in the high-boiling substance separating column was used instead of methacrylic acid employed in Example 1 and the gel-type strongly acidic cation exchange resin was filled instead of the porous strongly acidic cation exchange resin so that the overall exchange capacity became equal. The purity of the resulting purified methyl methacrylate was 99.99% by weight. An emulsion obtained by emulsion polymerizing the purified methyl methacrylate was clearly inferior in color stability to those formed in Examples 1 to 3.

During the 60-day continuous operation, the esterification reactor, fractionating column and other devices did not give rise to troubles ascribable to polymerized products. However, there was a problem with the performance of the cation exchange resin as a catalyst for esterification reaction. The conversion of methacrylic acid was gradually decreased, and when the operation was finished, it was decreased by 16% in comparison with that before operation.

COMPARATIVE EXAMPLE 3

The esterification reaction and purification were performed as in Example 1 except that 0.34 kg/hr of a 30% by weight sodium bisulfite aqueous solution was added to the methacrylic acid aqueous solution being fed to the extraction step and 12.5 kg/hr of toluene was used as an extraction solvent. The purity of the resulting purified methyl methacrylate was 99.99% by weight. An emulsion obtained by emulsion polymerizing the purified methyl methacrylate was clearly inferior in color stability to those formed in Examples 1 to 3.

During the 60-day continuous operation, the esterification reactor, fractionating column and other devices did not give rise to troubles ascribable to polymerized products However, there was a problem with the performance of the cation exchange resin as a catalyst for esterification reaction. The conversion of methacrylic acid was gradually decreased. When the operation was over, it was decreased by 9.1% in comparison with that before operation.

The amount of dimethylfuran in methyl methacrylate obtained in Examples 1 to 6 and Comparative Examples 1 to 3 and the color of the emulsion formed by emulsion polymerizing the methyl methacrylate in each of these examples were measured and the results are tabulated below.

|  | Amount of dimethylfuran (ppm) | Color of emulsion |
| --- | --- | --- |
| Example 1 | 20 |  |
| Example 2 | 20 |  |
| Example 3 | 18 |  |
| Example 5 | 30 |  |
| Example 6 | 15 |  |
| Comparative Example 1 | 60 | X |
| Example 2 | 40 | Δ |
| Example 3 | 38 | Δ |

The color of the emulsion was evaluated by vidual observation in accordance with the following three grades.

: good
Δ: somewhat bad
X: bad

What we claim is:

1. A process for producing a methacrylic ester which comprises catalytically oxidizing isobutylene, tert-butanol, methacrolein or isobutyl aldehyde in a vapor phase; removing light-boiling substances from the resulting reaction product by distillation or stripping; extracting methacrylic acid from the resulting methacrylic acid aqueous solution using a saturated chain aliphatic hydrocarbon having 6 to 9 carbon atoms as a solvent; recovering the solvent from the obtained solvent solution of methacrylic acid; esterifying the resulting methacrylic acid by the reaction of it with a lower aliphatic alcohol or a lower alicyclic alcohol having 1 to 12 carbon atoms using a porous strongly acidic cation exchange resin as a catalyst for esterification; and then subjecting the thus obtained esterification reaction product to a purification step.

2. The process of claim 1 wherein the porous strongly acidic cation exchange resin is a resin having a degree of crosslinking of 2 to 16%, a specific surface area of 0.2 to 50 $m^2/g$, a porosity of 0 to 1.0 ml/g and an average pore diameter of 100 to 600 Å.

3. The process of claim 1 or 2 wherein the alcohol is a lower aliphatic alcohol having 1 to 4 carbon atoms.

4. The process of claim 3 wherein the purification step comprises distilling the esterification reaction product by an evaporator, recycling the distillation bottoms of the evaporator to the esterification reaction step, cooling the distillate of the evaporator, separating the distillate into an oil phase and an aqueous phase, then separating the alcohol from the aqueous phase by distillation to recycle it to the esterification reaction step, and recovering the methacrylic ester from the oil phase by distillation.

5. The process of claim 4 wherein when recycling the distillation bottoms of the evaporator to the esterification reaction step, part or the whole of the distillation bottoms are distilled by a thin-layer evaporator to remove high-boiling impurities containing acetonylacetone, and the distillate is then recycled to the esterification reaction step.

6. The process of claim 1 wherein the solvent used in the extraction step includes an amount up to 50% by weight of another solvent selected from the group consisting of a methacrylic ester and an aromatic hydrocarbon.

7. The process of claim 1 wherein the esterification reaction is performed in a liquid phase at a temperature of 50 to 110° C. in a suspended bed of the catalyst.

8. The process of claim 1 wherein the esterification reaction is performed in a liquid phase at a temperature of 50 to 110° C. in a fixed bed of the catalyst.

* * * * *